United States Patent [19]

Rosen

[11] Patent Number: 5,446,050
[45] Date of Patent: Aug. 29, 1995

[54] AZABICYCLO AMIDES AND ESTERS AS 5-HT3 RECEPTOR ANTAGONISTS

[75] Inventor: Terry J. Rosen, East Lyme, Conn.
[73] Assignee: Pfizer Inc., New York, N.Y.
[21] Appl. No.: 856,978
[22] PCT Filed: Nov. 17, 1989
[86] PCT No.: PCT/US89/05097
 § 371 Date: May 27, 1992
 § 102(e) Date: May 27, 1992
[87] PCT Pub. No.: WO91/07402
 PCT Pub. Date: May 30, 1991
[51] Int. Cl.$^6$ .................. A61K 31/435; C07D 211/70
[52] U.S. Cl. .................... 514/305; 546/133; 546/137
[58] Field of Search ................. 546/133, 137; 514/305
[56] References Cited

U.S. PATENT DOCUMENTS

| | | | |
|---|---|---|---|
| 3,405,134 | 10/1968 | Judd | 260/294.3 |
| 3,563,995 | 2/1971 | Wellings | 260/293.4 |
| 4,467,095 | 8/1984 | Treves | 546/342 |
| 4,803,199 | 2/1989 | Donatsch et al. | 514/214 |
| 4,826,838 | 5/1989 | Richardson et al. | 514/210 |

FOREIGN PATENT DOCUMENTS

| | | |
|---|---|---|
| 0102283 | 3/1984 | European Pat. Off. . |
| 0221702 | 5/1987 | European Pat. Off. . |
| 0311724 | 4/1989 | European Pat. Off. . |
| 1293446 | 10/1972 | United Kingdom . |

OTHER PUBLICATIONS

CA 69(7): 27579 g Bender.
Bender, D. R. and Coffen, D. L., J. Org. Chem., 33(6), pp. 2504–2509, 1968.

*Primary Examiner*—Johann Richter
*Assistant Examiner*—Catherine Scalzo
*Attorney, Agent, or Firm*—Peter C. Richardson; Gregg C. Benson

[57] ABSTRACT

Novel azabicyclo amides and esters as antagonists at the 5-HT$_3$ receptor and useful as anti-emetic agents.

11 Claims, No Drawings

AZABICYCLO AMIDES AND ESTERS AS 5-HT3 RECEPTOR ANTAGONISTS

BACKGROUND OF THE INVENTION

This invention relates to novel azabicyclo amides and esters which are antagonists at the serotonin 5-HT$_3$ receptor and useful as anti-emetic agents in warm blooded animals, particularly the emesis associated with the anticancer drug cisplatin. The 5-HT$_3$ receptor antagonists of the present invention are also useful in the treatment of schizophrenia, migraine, anxiety, cognitive disorders, Alzheimer's disease, pain and gastrointestinal disorders, such as irritable bowel syndrome.

Compounds recognized for their ability to act as antagonists at the serotonin 5-HT$_3$ receptor sites are described in U.S. Pat. Nos. 4,593,034 and 4,749,718 and U.K. Patent Applications 2,125,398A, 2,166,726A, 2,166,727A, 2,166,728A and 2,193,633A.

SUMMARY OF THE INVENTION

The novel amides and esters of the present invention are of formula I and II:

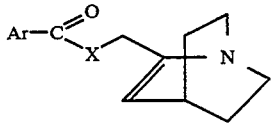

(I)

and

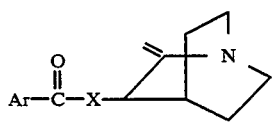

(II)

and a pharmaceutically acceptable acid addition salt, wherein Ar is an aromatic group such as phenyl, naphthyl, 3-indolyl, 3'-indazolyl, 1-methyl-3-indolyl, 2-methoxyphenyl or 2-methoxy-4-amino-5-chlorophenyl; and X is O or NH.

Preferred are the compounds of formula I, where X is NH and Ar is 3-indolyl, 3-indazolyl or 2-methoxy-4-amino-5-chlorophenyl.

A second preferred group of compounds are those of formula II wherein X is O and Ar is 3-indolyl or 1-methyl-3-indolyl.

Also considered part of the present invention are the useful intermediates of the formula

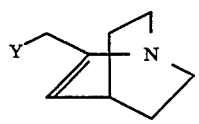

(III)

wherein Y is Cl, N$_3$, OH or NH$_2$.

The present invention also includes a method for treating emesis in a human being by administration of an anti-emetic amount of the compounds of formulae I and II and a pharmaceutical composition for said method comprising an effective amount of compounds of formulae I and II.

As previously indicated, the present invention embraces pharmaceutically acceptable salts of the biologically active compounds. Such salts are those which are non-toxic at the dosages administered. Since compounds of the invention contain basic groups, acid addition salts are possible. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate, glutamate, aspartate and saccharate salts.

DETAILED DESCRIPTION OF THE INVENTION

The compounds of formulae I and II wherein X is NH are prepared by acylation of the requisite amine with the appropriate acid as some reactive derivative. Such derivatives include acid halides, acid azides, acid cyanides, mixed acid anhydrides, active esters or active amides. Particularly preferred are acid halides, such as acid chlorides and active amides, such as acylimidazoles.

Acid chlorides are prepared by methods known to those skilled in the art and usually consist of reacting the acid with a chlorinating agent such as phosgene, thionyl chloride, phosphorous trichloride, phosphorus oxychloride, phosphorus pentachloride or. oxalylchloride.

Acyl imidazoles are readily prepared by reacting the appropriate acid with carbonyldiimidazole. The acyl imidazole can be generated in situ and used directly in the reaction, or it can be isolated prior to its use in the acylation reaction.

The acylation of the amine reagent is usually carried out in a reaction-inert solvent which is miscible with water. Such solvents include acetone, dimethylformamide, tetrahydrofuran, dimethylsulfoxide and dioxane.

In practice, equimolar amounts of the amine and acylating agent are combined in the appropriate solvent. Lesser or greater molar amounts of either reagents can be employed without changing the course of the reaction. When an acid chloride is employed as the acylating agent, it is preferred that a corresponding molar amount of acid scavenger be employed. Such scavengers include pyridine, triethylamine, etc.

Reaction temperature is not critical, and the acylation can readily be conducted at room temperature. At such a preferred reaction temperature, the reaction is substantially complete is about one to twelve hours.

The product is isolated by adding the water-miscible solvent to water or a salt solution thereof followed by extraction of the product with a water immiscible solvent such as methylene chloride or chloroform. On isolation, the product can be purified by classical methods such as recrystallization or column chromatography.

The compounds of formulae I and II wherein X is O are prepared by acylation of the appropriate alcohol with a reactive derivative of the requisite acid. Such derivatives are the same as those employed in the acylation of the amines as previously described. The preferred derivative is the acid chloride.

In practice, the acid chloride is added to a solution of an equimolar amount of the appropriate alcohol in a water soluble aprotic, reaction-inert solvent such as tetrahydrofuran. To facilitate the reaction it is preferred,that an alkali metal salt of the alcohol be employed. This can readily be prepared by treating a solution of the alcohol with sodium hydride or an alkyl lithium such as butyl lithium, prior to the addition of the acid chloride.

Reaction temperature is not critical, and the acylation can readily be carried out at room temperature. At such a preferred reaction temperature, the reaction is complete in five to seven hours.

The product is obtained and purified by the same procedure as previously described for the amide products of the present invention.

The starting alcohol leading to the compounds of formula II (X=O) is prepared by the sodium borohydride reduction of the corresponding commercially available ketone.

Treatment of the resulting alcohol with thionyl chloride leads to an unexpected rearrangement and formation of the compound of formula III (Y=Cl). Treatment of III (Y=Cl) with a tetra alkyl ammonium azide at low temperatures leads to the synthesis of III (Y=N$_3$). Reduction of this azide with lithium aluminum hydride provides the intermediate III (Y=NH$_2$).

Treatment of the mesylate of the alcohol required to form compounds of formula II (X=O) with a tetra alkyl ammonium azide gives rise to a mixture of two azides as shown:

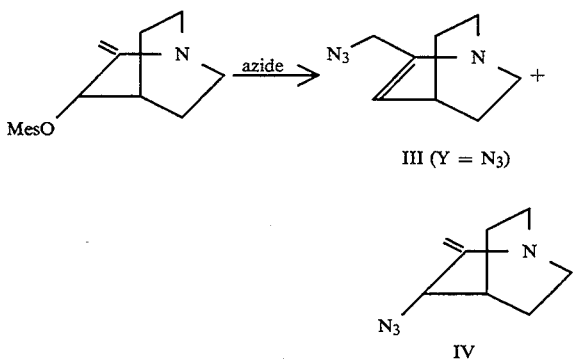

This mixture, which is comprised mainly of 2-methylene-3-azidoquinuclidine (Ca 2:1), can be reduced to a mixture of the corresponding amines. This mixture of amines can be used in the acylations previously described and the products subsequently separated and purified, or the mixture of amines can be converted to the respective t-butoxycarbonyl derivatives and separated. The separated t-butoxycarbonyl derivative can then be treated with dioxane saturated with hydrogen chloride resulting in the deblocking of the amine and isolation of the amine hydrochloride.

As previously mentioned, the compounds of the instant invention are antagonists of 5-hydroxytryptamine (5-HT) at the 5-HT$_3$ receptors. This property is demonstrated by their ability to antagonize the effects of 5-HT in the Bezold-Jarisch reflex [Richardson, et al., Nature 316, 126 (1985)] and their ability to bind to 5-HT receptors in brain tissue [Watling, et al., European J. Pharmacol. 149, 397 (1988)]. The compounds of the present invention are especially useful in controlling emesis due to administration of platinum anti-cancer agents. Evaluation of these compounds as anti-emetic agents against cisplastin uses the procedure in Cylys, Res. Commun. Chem. Pathol. Pharmacol., 23, 61 (1979).

The compounds of the present invention can be administered as antiemetic agents by either the oral or parenteral routes of administration, with the former being preferred for reasons of patient convenience and comfort. In general, these antiemetic compounds are normally administered orally in dosages ranging from about 5 mg to about 10 mg per kg of body weight per day and 0.1 mg to about 1.0 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous Suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

EXAMPLE 1

N-(2,3-Dehydroquinuclidin-2-ylmethyl)-2-methoxy-4-amino-5-chlorobenzamide (I: Ar=2—CH$_3$O—4—NH$_2$—5—Cl—C$_6$H$_2$; X=NH)

Under a nitrogen atmosphere, in a round-bottom flask were placed 363 mg (1.8 mmol) of 2-methoxy-4-amino-5-chlorobenzoic acid and two mL of tetrahydrofuran. To the system was added 586 mg (3.6 mmol) of carbonyl diimidazole. The reaction mixture was stirred for 40 minutes, partitioned between chloroform and water and extracted with chloroform. The organic phase was dried (Na$_2$SO$_4$) and concentrated with a rotary evaporator. To the system was added 250 mg (1.8 mmol) of 2-aminomethyl-2,3-dehydroquinuclidine in two mL tetrahydrofuran, and the reaction mixture was stirred at room temperature overnight. The reaction mixture was partitioned between chloroform and saturated aqueous sodium bicarbonate and extracted with chloroform. The organic phase was dried ($Na_2SO_4$) and concentrated, and the crude product was purified by flash column chromatography (25 g of silica gel) using 1:9 methanol/chloroform as the eluant to obtain 133 mg of white solid. This material was triturated with ether to obtain 85 mg of pure product as a white solid, mp 202°–204° C. $^1$HNMR ($CDCl_3$) delta 1.48 (m, 2H), 1.58 (m, 2H), 2.54 (m, 3H), 2.92 (m, 2H), 3.86 (s, 3H), 3.99 (d, 2H, J=6), 6.24 (s, 1H), 6.28 (d, 1H, J=6), 7.22 (s, 1H) HRMS: Calcd for $C_{16}H_{20}N_3O_2Cl^{35}$: 321.1244. Found: 321.1198.

EXAMPLE 2

Starting with the appropriate reagents and using the procedure of Example 1, the following compounds were prepared:

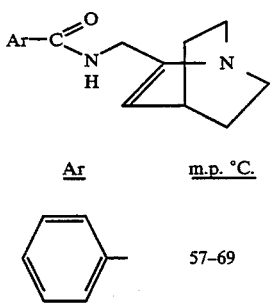

| Ar | m.p. °C. |
|---|---|
| phenyl | 57–69 |

$^1$HNMR ($CDCl_3$) delta 1.34 (m,2H), 1.52 (m, 2H), 2.50 (m, 3H), 2.90 (m, 2H), 3.98 (d, 2H, J=6), 6.29 (d, 1H, J=6), 7.34 (m, 3H), 7.72 (d, 2H, J=6). HRMS: Calcd. for $C_{15}H_{18}N_2O$: 242.1419. Found: 242.1388. Calcd. for $C_{15}H_{18}N_2O \times \frac{1}{2} H_2O$: C, 71.67, H, 7.61, N, 11.14. Found: C, 71.56, H, 7.70, N, 11.03.

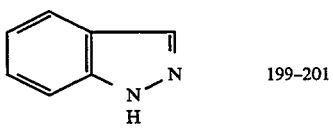

199–201

$^1$HNMR ($CDCl_3$) delta 1.64 (m, 4H), 2.74 (m, 3H), 3.12 (m, 2H), 4.08 (d, 2H, J=7), 6.68 (d, 1H, J=6), 7.20 (m, 1H), 7.34 (t, 1H, J=6), 7.42 (d, 1H, J=6), 8.42 (d, 1H, J=6). HRMS: Calcd. for $C_{16}H_{14}N_4O$: 282.1481. Found: 282.1487.

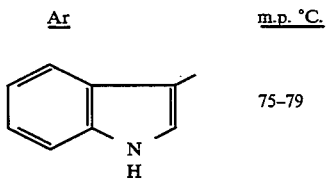

| Ar | m.p. °C. |
|---|---|
| indolyl | 75–79 |

$^1$HNMR ($CDCl_3$) delta 1.38 (m, 2H), 1.54 (m, 2H), 2.54 (m, 3H), 2.82 (m, 2H), 4.06 (d, 2H, J=6), 6.36 (d, 1H, J=7), 7.18 (m, 2H), 7.38 (m, 1H), 7.66 (d, 1H, J=2), 7.96 (m, 1H). HRMS: Calcd. for $C_{17}H_{19}N_3O$: 281.1528. Found: 281.1552.

EXAMPLE 3

1-Methylindole-3-(2-methylenequinuclidin-3-yl)carboxamide (II: Ar=1-methyl-3-indolyl; and X=NH)

Under a nitrogen atmosphere, in a round-bottom flask were placed 0.36 mmol of a mixture of 2-aminomethyl-2,3-dehydroquinuclidine and 3-amino-2-methylenequinuclidine (ca 1:2) and 0.5 mL of tetrahydrofuran. To the system were added 105 mg (0.54 mmol) of 20 3-chlorocarbonyl-1-methylindole and 54 mg (0.075 mL, 0.54 mmol) of triethylamine. The reaction mixture was stirred at room temperature for ca. one hour, diluted with chloroform, washed with saturated aqueous sodium bicarbonate, dried ($Na_2SO_4$) and concentrated with a rotary evaporator. The crude material was subjected to flash column chromatography (10 g of silica gel) to obtain 30 mg of the desired product. This material was dissolved in ethyl acetate and hydrogen chloride was bubbled through the solution. The solution was concentrated with a rotary evaporator to obtain 22 mg of the corresponding hydrochloride as a tan solid, mp 160°–167° C. $^1$HNMR (DMSO-$d_6$) delta 1.84 (m, 1H), 2.02 (m, 2H), 2.26 (m, 2H), 3.25 (m, 3H), 3.88 (s, 3H), 5.06 (m, 1H), 5.46 (s, 1H), 5.94 (s, 1H), 7.23 (m, 2H), 7.54 (d, 1H, J=7), 8.16 (d, 1H, J=7), 8.26 (s, 1H), 8.37 (d, 1H, J=7). HRMS (free base): Calcd. for $C_{18}H_{21}N_3O$: 295.1684. Found: 295.1683.

EXAMPLE 4

N-(2-Methylenequinuclidin-3-yl)-2-methoxy-4-amino-5-chlorobenzamide (II: Ar=2—$CH_3O$—4—$NH_2$—5—Cl—$C_6H_2$; and X=NH)

The titled amide product was prepared in a similar manner and has the following spectral properties: $^1$HNMR ($CDCl_3$) delta 1.44 (m, 1H), 1.68 (m, 3H), 2.18 (m, 1H), 2.98 (m, 4H), 3.84 (s, 3H), 4.68 (d, 1H, J=8), 4.95 (d, 1H, J=2), 5.08 (d, 1H, J=2), 6.28 (s, 1H), 7.90 (d, 1H, J=8). HRMS: Calcd. for $C_{16}H_{20}N_3O_2Cl^{35}$: 321.1244. Found: 321.1235.

EXAMPLE 5

2-Methylenequinuclidin-3-yl indole-3-carboxylate (II: Ar=3-indolyl; and X=O)

Under a nitrogen atmosphere, in a round-bottom flask were placed 500 mg (3.1 mmol) of indole-3-carboxylic acid and three mL of tetrahydrofuran. To the system was added 0.30 mL (3.4 mmol) of oxalyl chloride over a period for five minutes, and the reaction mixture was stirred at room temperature for 1.5 hours and concentrated with a rotary evaporator. In a separate flask, under a nitrogen atmosphere, were placed 366 mg (2.63 mmol) of the alcohol 2-methylene-3-quinuclidinol and three mL of tetrahydrofuran. To this solution, cooled to 0° C., was added slowly 1.04 mL (2.6 mmol) of 2.5M n-butyllithium in hexanes, and the mixture was stirred for five minutes and concentrated. The residue was dissolved in one mL of tetrahydrofuran and added to the acid chloride prepared above (two one mL rinses). The mixture was stirred at room temperature for five hours and partitioned between chloroform and saturated aqueous sodium bicarbonate. The layers were separated, and the aqueous phase was extracted with three portions of chloroform. The combined organic fractions were dried ($Na_2SO_4$) and concentrated. The crude material was purified by flash column chromatography (50 g of silica gel) using 1:19 methanol/- chloroform as the eluant to obtain 435 mg of white foam which solidified, mp 99°–109° C. (dec.) $^1$HNMR (CDCl$_3$) delta 1.54 (m, 1H), 1.76 (m, 2H), 2.04 (m, 1H), 2.34 (m, 1H), 3.10 (m, 5H), 5.17 (s, 1H), 5.32 (s, 1H), 5.68 (s, 1H), 7.26 (m, 1H), 7.41 (m, 1H), 7.84 (m, 1H), 8.14 (s, 1H). HRMS: Calcd. for C$_{17}$H$_{18}$N$_2$O$_2$:282.1369. Found: 282.1358.

EXAMPLE 6

Employing the procedure of Example 5 and starting with the requisite reagents, the following compounds were prepared:

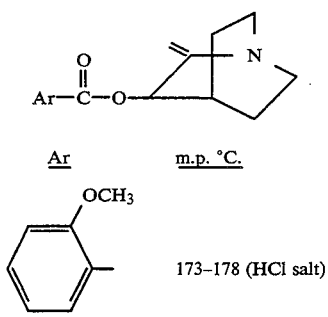

| Ar | m.p. °C. |
|---|---|
| 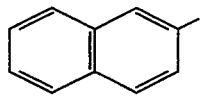 OCH$_3$ | 173–178 (HCl salt) |

$^1$HNMR (DMSO-d$_6$) delta 2.0 (m, 4H), 3.44 (m, 5H), 3.86 (s, 3H), 5.62 (s, 1H), 5.76 (m, 1H), 5.88 (m, 1H), 7.05 (t, 1H, J=7), 7.19 (d, 1H, J=7), 7.60 (t, 1H, J=7), 7.74 (d, 1H, J=7). HRMS: Calcd. for C$_{16}$H$_{15}$NO$_3$: 273.1365. Found: 273.1340.

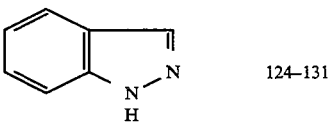 —

$^1$HNMR (CDCl$_3$) delta 2.02 i(m, 2H), 2.16 (m, 1H), 2.40 (m, 1H), 2.71 (m, 1H), 3.48 (m, 2H), 3.64 (m, 2H), 5.70 (m, 1H), 5.86 (m, 1H), 6.i48 (s, 1H), 7.62 (m, 2H), 7.94 (m, 4H), 8.58 (s, 1H). HRMS: Calcd. for C$_{19}$H$_{19}$NO$_2$: 293.1416. Found: 293.1431.

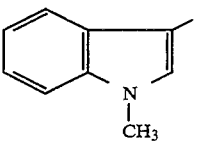 124–131

$^1$HNMR (CDCl$_3$) delta 1.58 (m, 1H), 1.82 (m, 2H), 2.06 (m, 1H), 2.42 (m, 1H), 3:12 (m, 4H), 5.22 (s, 1H), 5.37 (s, 1H), 5.85 (s, 1H), 7.30 (t, 1H, J=8), 7.44 (t, 1H, J=8), 7.78 (d, 1H, J=8) 8.14 (d, 1H, J=8). HRMS: Calcd. for C$_{16}$H$_{17}$N$_3$O$_2$: 283.1321. Found: 283.1302.

| Ar | m.p. °C. |
|---|---|
| 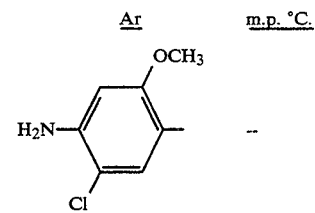 | — |

$^1$HNMR (CDCl$_3$) delta 1.48 (s, 1H), 1.70 (m, 2H), 1.94 (m, 1H), 2.24 (m, 1H), 3.02 (m, 4H), 3.82 (s, 3H), 5.04 (s, 1H), 5.28 (s, 1H), 5.53 (s, 1H), 7.23 (s, 1H), 7.76 (s, 1H).

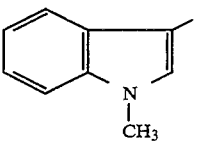 228 (dec.)

$^1$HNMR (DMSO-d$_6$) delta 2.00 (m, 3H), 2.24 (m, 1H), 3.46 (m, 5H), 3.92 (s, 3H), 5.i65 (s, 1H), 5.84 (s, 1H), 5.98 (s, 1H), 7.31 (m, 2H), 7.61 (d, 1H, J=7), 8.00 (d, 1H, J=7), 8.30 (s, 1H). HRMS: Calcd. for C$_{18}$H$_{20}$N$_2$O$_2$: 296.1525. Found: 296.1504.

EXAMPLE 7

2,3-Dehydroquinuclidin-2-ylmethyl indole-3-carboxylate (I: Ar=3-indolyl; and X=O)

Under a nitrogen atmosphere, in a round-bottom flask are placed 20 mmol of potassium carbonate and 7 mL of water. To the system is added 10 mmol of the product of preparation B1 in 3 mL of tetrahydrofuran, and the mixture is stirred until thin layer chromatography indicates that no starting chloride remains. The mixture is diluted with water and extracted with several portions of methylene chloride. The combined dichloromethane fractions are dried (Na$_2$SO$_4$) and concentrated with a rotary evaporator, and the crude product is subjected to flash column chromatography to obtain 2-hydroxymethyl-2,3-dehydroquinuclidine (III, Y=OH). The procedure of Example 5 is repeated, replacing 2-methylene-3-quinuclidinol with III (Y=OH), to obtain the title compound.

PREPARATION A

2-Methylene-2-Quinuclidinol

Under a nitrogen atmosphere, in a round-bottom flask were placed 16.7 g (122 mmol) of commercial 2-methylene-3-quinuclidinome and 250 mL of methanol. To this stirring solution Was added 4.75 g (125 mmol) of sodium borohydride in portions over a period of 10 minutes. The reaction mixture was stirred at room temperature for 20 minutes, 200 mL of ethyl acetate was added to the system and the mixture was stirred for 10 minutes. To the system was added cautiously and slowly saturated aqueous sodium bicarbonate. To the mixture were added additional water and ethyl acetate, the layers were separated and the aqueous phase was extracted with ethyl acetate. The combined organic fractions were dried (Na$_2$SO$_4$) and concentrated. The crude material was purified by flash column chromatography (400 g of silica gel) using 1:9 methanol/chloroform as the eluant to obtain 3.8 g of product, mp 90°–92° C. HNMR (CDCl$_3$) delta 1.32 (m, 1H), 1.46 (m, 1H), 1.62 (m, 1H), 1.86 (m, 2H), 2.68 (m, 1H), 2.88 (m, 3H), 4.17 (d, 1H, J=2), 4.96 (d, 1H, J=2), 5.08 (d, 1H, J=2). HRMS: Calcd. for C$_8$H$_{13}$NO: 139.0998. Found: 139.0998. Calcd. for C$_8$H$_{13}$NO: C, 69.03, H, 9.41, N, 10.06. Found: C, 68.63, H, 9.24, N, 10.09.

PREPARATION B

2-Aminomethyl-2,3-dehydroquinuclidine 1. 2-chloromethyl-2,3-dehydroquinuclidine

Under a nitrogen atmosphere, in a round-bottom flask were placed two g (14 retool) of the product of Preparation A and 5 mL of methylene chloride, and the system was immersed in an ice bath. To the system was added 5.25 mL (72 mmol) of thionyl chloride dropwise over a period of 5 minutes. The ice bath was allowed to expire, and the reaction mixture was stirred at room temperature overnight. The reaction mixture was concentrated with a rotary evaporator, and 2N aqueous sodium hydroxide was added to the system. To the system was added water and the mixture was extracted with two portions of methylene chloride. The combined organic fractions were dried and concentrated to afford 1.9 g of the titled product as a yellow oil. $^1$HNMR (CDCl$_3$) delta 1.38 (m, 2H), 1.56 (m, 2H), 2.56 (m, 3H), 2.94 (m, 2H), 3.96 (s, 2H), 6.48 (d, 1H, J=6). Calcd. for C$_8$H$_{12}$ClN×$\frac{1}{2}$H$_2$O: C, 57.65, H, 7.86, N, 8.40. Found: C, 57.92, H, 7.92, N, 8.17.

2. 2-azidomethyl-2,3-dehydroquinuclidine

Under a nitrogen atmosphere, in a round-bottom flask immersed in an ice/acetone bath were placed 3 g (19 mmol) of the product of Preparation B1 30 mL of acetonitrile, 2.65 mL (19 mmol) of triethylamine and 10 g (35 mmol) of tetra-n-butylammonium azide, and the reaction mixture was stirred for two hours, the temperature of the cold bath gradually rising to −5° C. The reaction mixture was poured into cold saturated aqueous sodium bicarbonate and extracted with cold ethyl acetate. The ethyl acetate solution was washed with three portions of cold aqueous sodium bicarbonate, dried (Na$_2$SO$_4$) and concentrated to obtain 8 g of crude product. This material was dissolved in cold ether/ethyl acetate and washed with five portions of cold aqueous sodium bicarbonate, dried (Na$_2$SO$_4$) and concentrated (rotary evaporator, cold water bath) to obtain 1.8 g of the allylic azide product as a yellow oil which was used immediately for the next transformation. $^1$HNMR (CDCl$_3$) delta 1.32 (m, 2H), 1.50 (m, 2H), 2.28 (m, 2H), 2.94 (m, 2H), 3.26 (m, 1H), 3.65 (s, 2H), 6.37 (d, 1H, J=7). HRMS Calcd. for C$_8$H$_{12}$N$_4$: 164.1061. Found: 164.1025.

3. 2-Aminomethyl-2,3-dehydroquinuclidine

Under a nitrogen atmosphere, in a round-bottom flask were placed 22 mL (22 mmol) of 1M lithium aluminum hydride tetrahydrofuran, and the system was cooled in a dry ice/acetone bath. To the system was added dropwise over a period of ca. two minutes a solution of 1.8 g (11 mmmol) of the compound of Preparation B2 in 7.8 mL of tetrahydrofuran and the cold bath was replaced with an ice/acetone bath. The reaction mixture was stirred for 30 minutes, the cold bath was removed and the mixture was stirred for an additional period of 30 minutes. The system was immersed in an ice/acetone bath, and 10 mL of 2N aqueous sodium hydroxide was added slowly and cautiously to the mixture. The system was removed from the cold bath, and the reaction mixture was stirred for 10 minutes. Sodium sulfate was added to the mixture, and after 15 minutes the solids were removed by suction filtration. The filtrate was concentrated with a rotary evaporator to obtain 1.67 g of product as a colorless oil which was used in subsequent transformations without further purification. $^1$HNMR (CDCl$_3$) delta 1.34 (m, 2H), 1.50 (m, 2H), 2.48 (m, 3H), 2.90 (m, 2H), 3.21 (s, 2H), 6 17 (d, 1H, J=7). Mass spectrum, m/z 138 (parent).

PREPARATION C

3-Amino-2-methylenequinuclidine Hydrochloride 1. 2-methylene-3-quinuclidinol mesylate Under a nitrogen atmosphere, in a round-bottom flask were placed 8 g (58 mmol) of the alcohol of Preparation A and 60 mL of tetrahydrofuran. To the system (cooled in an ice/acetone bath) was added 17.9 mL (128 mmol) of triethylamine followed by 5.13 mL (66 mmol) of methanesulfonyl Chloride over a period of 15 minutes. The mixture was gradually warmed to room temperature and stirred overnight. The reaction mixture was partitioned between 2N aqueous sodium hydroxide and chloroform, the layers were separated and the aqueous phase was extracted with chloroform. The combined chloroform fractions were dried (Na$_2$SO$_4$) and concentrated (rotary evaporator). The crude material was purified by flash column chromatography (300 g of silica gel) using 1:9 methanol/chloroform as the eluant to obtain 5.3 g of the desired product. $^1$HNMR (CDCl$_3$) delta 1.48 (m, 2H), 1.68 (m, 1H), 1.84 (m, 1H), 2.28 (m, 1H), 2.76 (m, 1H), 2.94 (m, 3H), 3.04 (s, 3H), 5.08 (d, 1H, J=5), 5.14 (s, 1H), 5.24 (d, 1H, J=5).

2. Mixture of 2-methylene-3-azidoquinuclidine and 20azidomethyl-2,3-dehydroquinuclidine Under a nitrogen atmosphere were placed 5.3 g (24 mmol) of the product of Preparation C1 and 65 mL of acetonitrile. To the system was added 13.7 g (48 mmol) of tetra-n-butylammonium azide, and the reaction mixture was stirred at 55° C. for 90 minutes and at room temperature overnight. The reaction mixture was partitioned between saturated aqueous sodium bicarbonate and chloroform, the layers were separated and the aqueous phase was extracted with chloroform. The combined chloroform fractions were dried (Na$_2$SO$_4$) and concentrated with a rotary evaporator. The crude material was purified by flash column chromatography (650 g of silica gel) using 1:9 methanol/chloroform as the eluant to obtain 5.5 g of colorless oil. This material was dissolved in chloroform and extracted with dilute aqueous hydrochloric acid. The aqueous extract was adjusted to a pH of ca. 7.5 and extracted with three portions of chloroform. The combined chloroform extracts were dried (Na$_2$SO$_4$) and concentrated to afford 3.46 of a mixture (ca. 2:2) of the titled azides, respectively.

3. Mixture of 2-methylene-3-aminoquinuclidine and 2-aminomethyl-2,3-dehydroquinuclidine Under a nitrogen atmosphere, in a round-bottom flask were placed 42 mL (42 mmol) of 1M lithium aluminum hydride in tetrahydrofuran. The system was cooled to −78° C., and the azide mixture prepared above (3.46 g, 21.0 mmol) in 15 mL of tetrahydrofuran was added to the system dropwise. The mixture was stirred for 30 minutes, and the cold bath was replaced with an ice/acetone bath. The mixture was stirred for 30 minutes at room temperature, the cold bath was removed and the mixture was stirred at room temperature for one hour. The system was cooled in an ice/acetone bath and 20 mL of 2N aqueous sodium hydroxide was added cautiously and slowly to the system. To the system was added Na$_2$SO$_4$, the mixture was stirred for one hour, the solids were moved by suction filtration and filtrate was concentrated with a rotary evaporator to obtain 1.9 g of a mixture of the titled amines as a pale yellow oil. This mixture was used without further purification to obtain amides.

4. 2-methylene-3-aminoquinuclidine hydrochloride

Under a nitrogen atmosphere, in a round-bottom flask were placed 50 mg (0.36 mmol) of the mixture of amines from Preparation C2 and 0.5 mL of di-tert-butyldicarbonate, and the reaction mixture was stirred at room temperature for three days. The mixture was partitioned between dichloromethane and saturated aqueous sodium bicarbonate, and the layers were separated. The aqueous phase was extracted with dichloromethane, and the combined organic fractions were dried ($Na_2SO_4$) and concentrated with a rotary evaporator. The crude material was subjected to flash column chromatography (15 g of silica gel) to obtain 46 mg of the t-butoxycarbonyl derivative of 2-methylene-3-aminoquinuclidine $^1$HNMR ($CDCl_3$) delta 1.46 (s, 9H), 1.68 (m, 3H), 2.09 ( s, 1H), 2.92 (m, 4H), 4.26 (m, 1H), 4.76 (m, 1H), 4.95 (s, 1H), 5.09 (s, 1H). Mass spectrum, m/z 248 (parent) and 13 mg of the t-butoxycarbonyl derivative of 2-aminomethyl-2,3-dehydroquinuclidine. $^1$HNMR ($CDCl_3$) delta 1.44 (m, 10H), 1.6 (m, 2H), 2.16 (m, 1H), 2.52 (m, 3H), 2.92 (m, 2H), 3.70 (m, 2H), 6.28 (d, 1H, J=7). Mass spectrum, m/z 248 (parent).

Under a nitrogen atmosphere, in a round-bottom flask were placed 29 mg (0.12 mmol) of the t-butoxycarbonyl derivative of 2-methylene-3-aminoquinuclidine and 0.8 mL of dioxane saturated with hydrogen chloride. The mixture was stirred at room temperature for 90 minutes and concentrated with a rotary evaporator to obtain 34 mg of the hydrochloride salt of the product as a white solid. $^1$HNMR (DMSO-$d_6$) delta 1.92 (m, 3H), 2.10 (m, 1H), 2.44 (m, 1H), 3.24 (m, 1H), 3.46 (m, 3H), 4.30 (m, 1H), 5.93 (s, 1H), 6.03 (s, 1H). Mass spectrum, m/z 238 (parent).

I claim:

1. A compound of the formulae

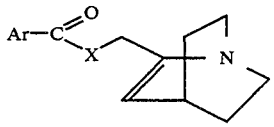 (I)

and

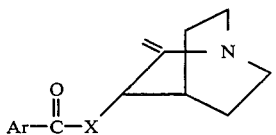 (II)

and a pharmaceutically acceptable acid addition salt thereof wherein Ar is phenol, naphthyl, 3-indolyl, 3-indazolyl, 1-methyl-3-indolyl, 2-methoxyphenyl or 2-methoxy-4-amino-5-chlorophenyl; and X is O or NH.

2. A compound of claim 1, formula I, wherein X is NH.

3. The compound of claim 2, wherein Ar is 3-indolyl.

4. The compound of claim 2, wherein Ar is 3-indazolyl.

5. The compound of claim 2, wherein Ar is 2-methoxy-4-amino-5-chlorophenyl.

6. A compound of claim 1, formula II, wherein X is O.

7. The compound of claim 6, wherein Ar is 3-indolyl.

8. The compound of claim 6, wherein Ar is 1-methyl-3-indolyl.

9. A compound of the formula

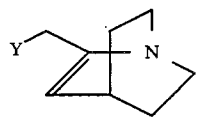 (III)

wherein Y is Cl, $N_3$ or $NH_2$.

10. A method for treating emesis in a human being which comprises administering to said human being an anti-emetic effective amount of a compound according to claim 1.

11. A pharmaceutical composition comprising an anti-emetic effective amount of a compound according to claim 1 and a pharmaceutically acceptable diluent or carrier.

* * * * *